US00PP37645P3

(12) United States Plant Patent
Leiber

(10) Patent No.: US PP37,645 P3
(45) Date of Patent: Aug. 25, 2026

(54) GARLIC PLANT NAMED 'Slamka'

(50) Latin Name: ***Allium sativum* var. *ophioscorodon***
Varietal Denomination: Slamka

(71) Applicant: Katrina Anne Leiber, Franksville, WI (US)

(72) Inventor: Katrina Anne Leiber, Franksville, WI (US)

( * ) Notice: Subject to any disclaimer, the term of this patent is extended or adjusted under 35 U.S.C. 154(b) by 0 days.

(21) Appl. No.: 18/831,654

(22) Filed: Jul. 7, 2025

(65) Prior Publication Data

US 2026/0053078 P1 Feb. 19, 2026

Related U.S. Application Data

(60) Provisional application No. 63/732,456, filed on Aug. 19, 2024.

(51) Int. Cl.
*A01H 5/06* (2018.01)
*A01H 5/00* (2018.01)
*A01H 6/04* (2018.01)

(52) U.S. Cl.
USPC ..... Plt./258
CPC ..... *A01H 6/04* (2018.05); *A01H 5/00* (2013.01)

(58) Field of Classification Search
USPC ..... Plt./258
CPC ... A01H 5/12; A01H 5/04; A01H 5/08; A01H 5/00; A01H 6/04; A01H 5/06
See application file for complete search history.

(56) References Cited

PUBLICATIONS

International Code of Nomenclature for Cultivated Plants Ninth Edition 2016, 7 introductory pages and p. 29. (Year: 2016).*

* cited by examiner

*Primary Examiner* — June Hwu

(57) ABSTRACT

A new and distinct variety of garlic plant, *Allium sativum* var. *ophioscorodon*, named 'Slamka', is characterized by its exceptional disease and pest resistance, high yields, minimal cultivation requirements, and robust hardiness. Originating from a strain cultivated for more than a century in Southeastern Wisconsin, this variety is particularly well-suited to temperate climates and has shown consistent resistance to common garlic diseases over an eight-year observation period. These traits make it an ideal choice for growers in temperate regions, particularly Southeastern Wisconsin. 'Slamka' has not been tested in other regions, and its ability to thrive outside of Southeastern Wisconsin is unknown.

16 Drawing Sheets

Latin name of the genus and species of the claimed plant: *Allium sativum* var. *ophioscorodon.*

Variety denomination: 'Slamka'.

BACKGROUND

Garlic cultivation has a rich history, with evidence of its use and cultivation spanning thousands of years across various cultures. Despite its long history, garlic crops are vulnerable to numerous diseases and pests, which can significantly impact yields. To mitigate these challenges, garlic farmers may rely on pesticides and costly disease management techniques.

By addressing these challenges, the claimed garlic variety 'Slamka' provides a sustainable option for growers seeking high-yield, low-maintenance garlic with natural disease resistance. The present invention relates to a new and distinct garlic plant variety discovered under cultivation, as described herein. It offers robust disease and pest resistance, minimal cultivation requirements, high yields, and exceptional overall resilience.

SUMMARY OF THE INVENTION

'Slamka' is a new and distinct variety of *Allium sativum* var. *ophioscorodon* that was discovered among garlic plants grown in a cultivated agricultural planting under standard garlic production practices in Southeastern Wisconsin, and selected from among surrounding garlic plants due to the presence of distinguishing characteristics not observed in those surrounding plants, and thereafter asexually reproduced by vegetative propagation. The parents of the claimed plant variety are unknown.

Following discovery, the claimed variety has been asexually reproduced by vegetative propagation using cloves under cultivated conditions in Southeastern Wisconsin. After successive generations of asexual reproduction, the distinguishing characteristics of the claimed plant variety have been shown to be stable and reproduced true to type. The variety has been propagated without the use of pesticides or chemical treatments and has demonstrated consistent overwinter survival and normal vegetative growth under the regional climate and soil conditions under cultivation.

Under the described cultivation conditions, the claimed variety has been observed to perform optimally in hilled rows topped with weed barrier and typically does not require supplemental watering except during germination and periods of extreme drought. During multiple growing seasons under standard field conditions in Southeastern Wisconsin, no observable symptoms of disease or pest infestation were detected. These observations demonstrate the suitability of the claimed variety for cultivation in this region and in similar climates where comparable environmental conditions exist.

BRIEF DESCRIPTION OF THE DRAWINGS

The attached photographs are of 'Slamka' grown during the 2023-2024 growing season in Southeastern Wisconsin. The photographs show the overall appearance of the new variety 'Slamka'. The colors in the photos are as accurate as reasonably possible but may differ slightly from the true color of the plant.

DETAILED DESCRIPTION OF THE INVENTION

Figure 1:
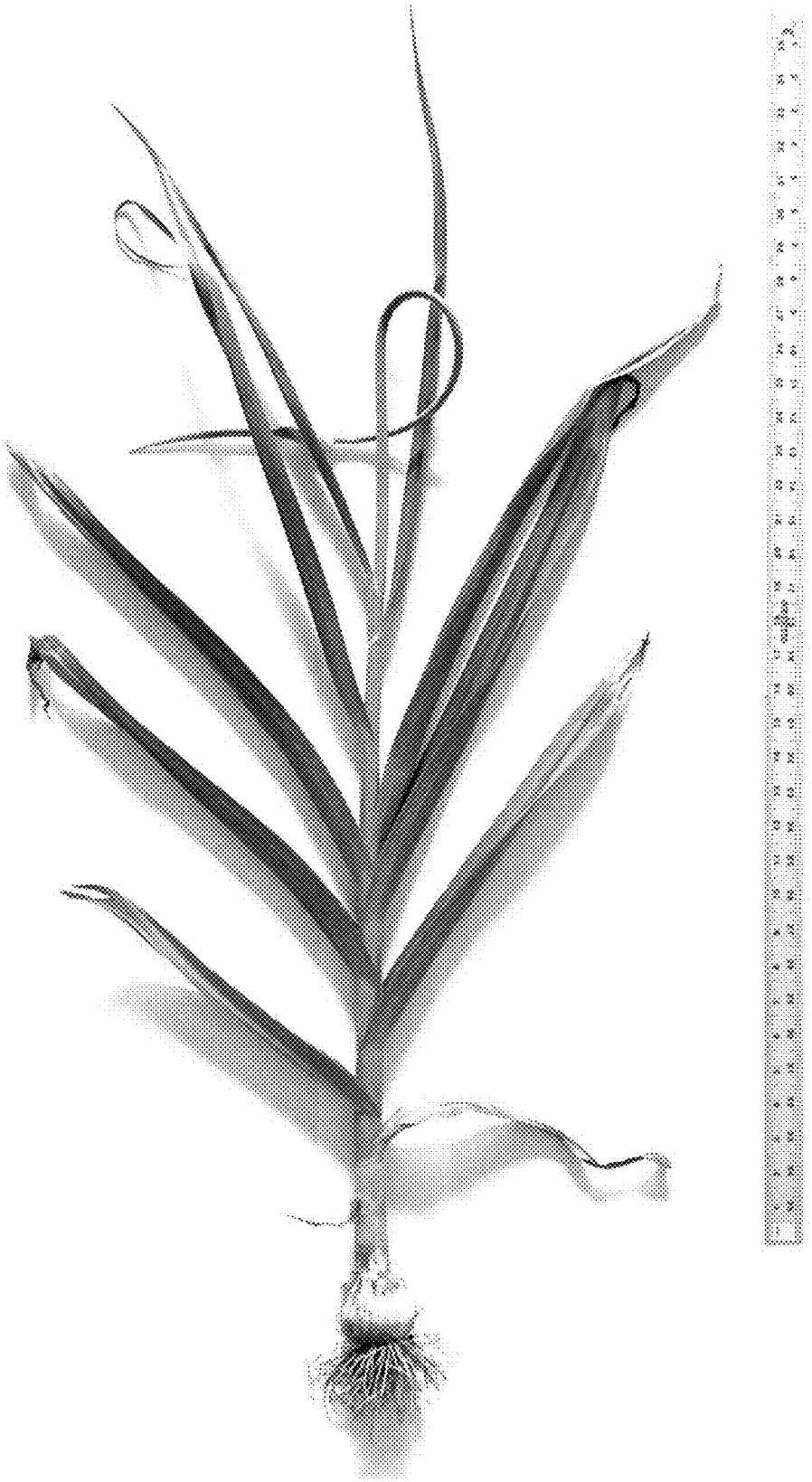
FIG. 1: Garlic plant pulled 9.5 months after planting, displayed next to a yardstick.
Figure 2:
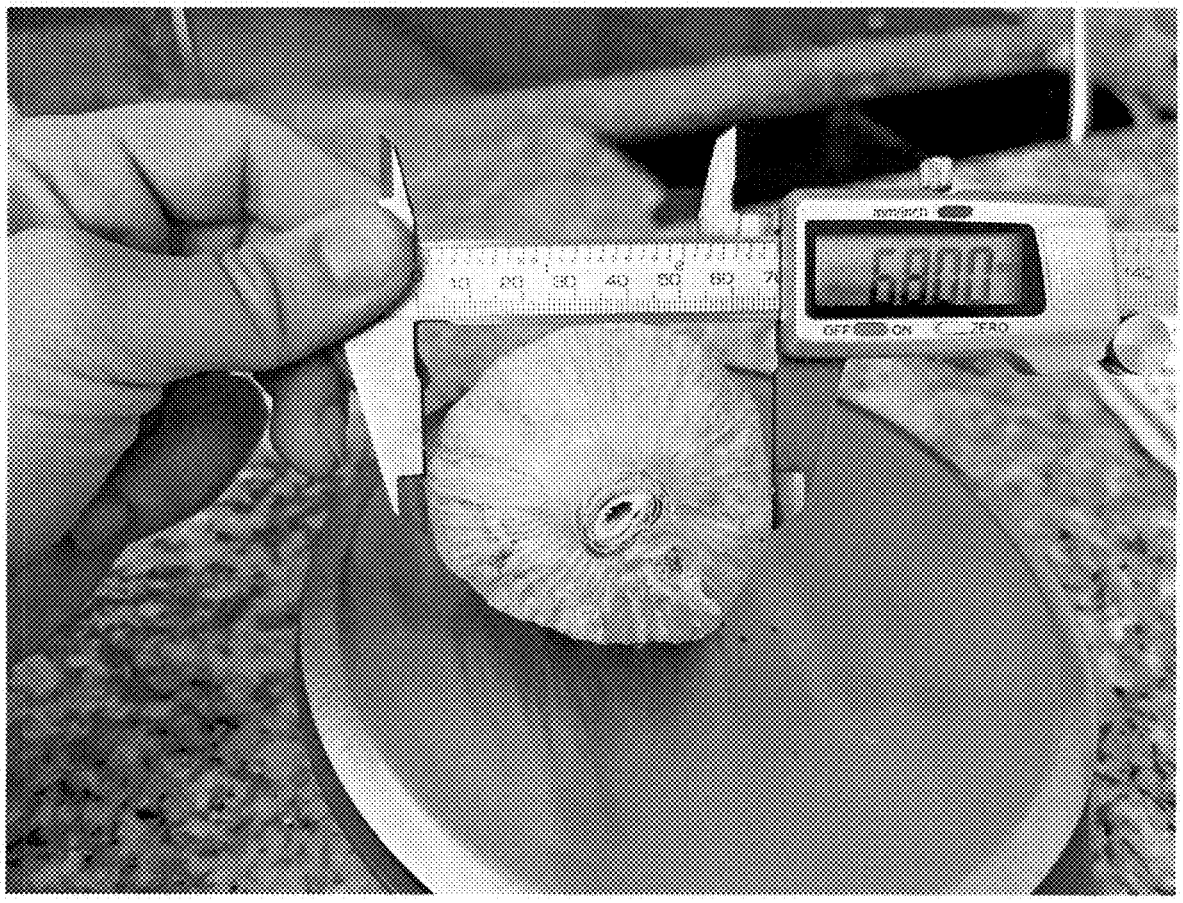
FIG. 2: 'Slamka' bulb, measuring 6.8 cm in diameter.
Figure 3:
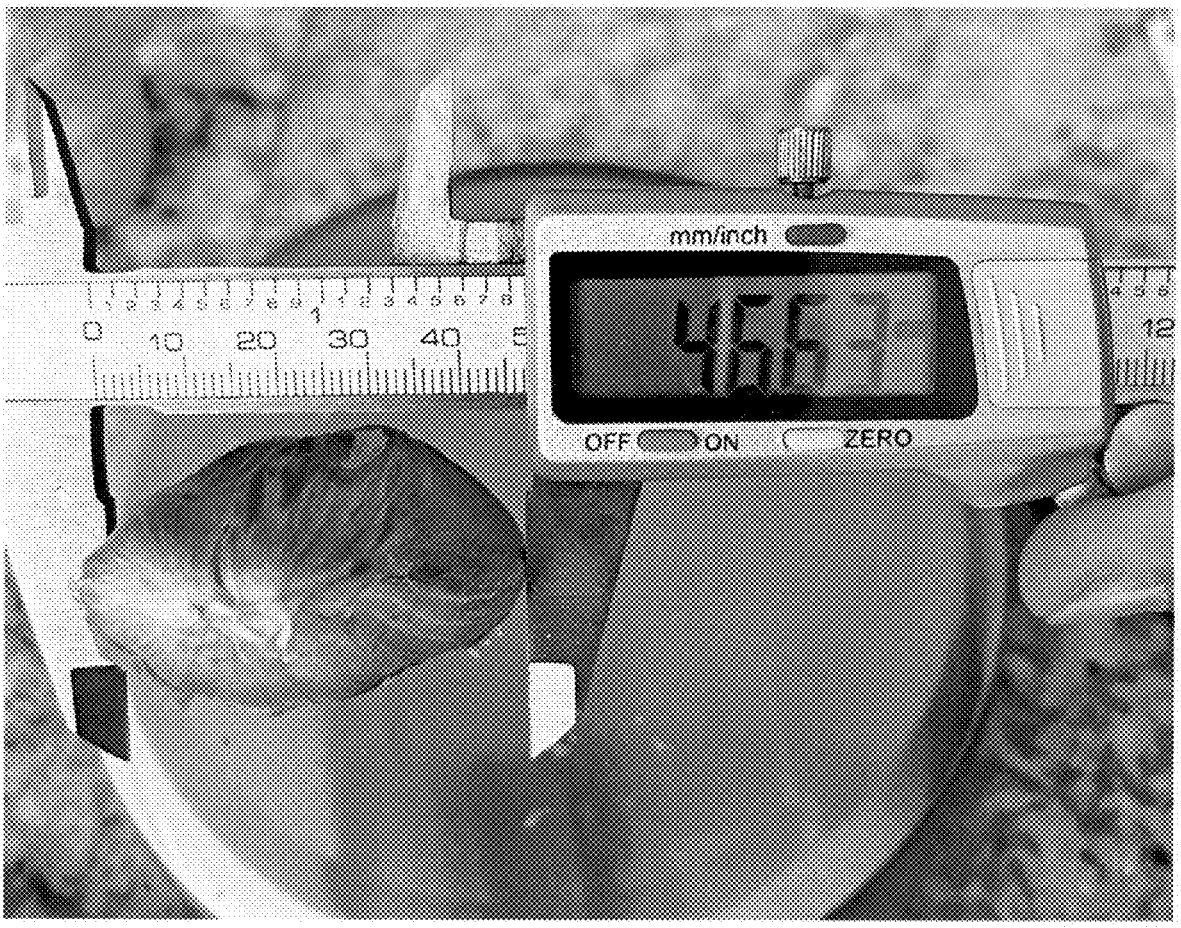
FIG. 3: A larger clove from 'Slamka', measuring 4.66 cm in width.
Figure 4:
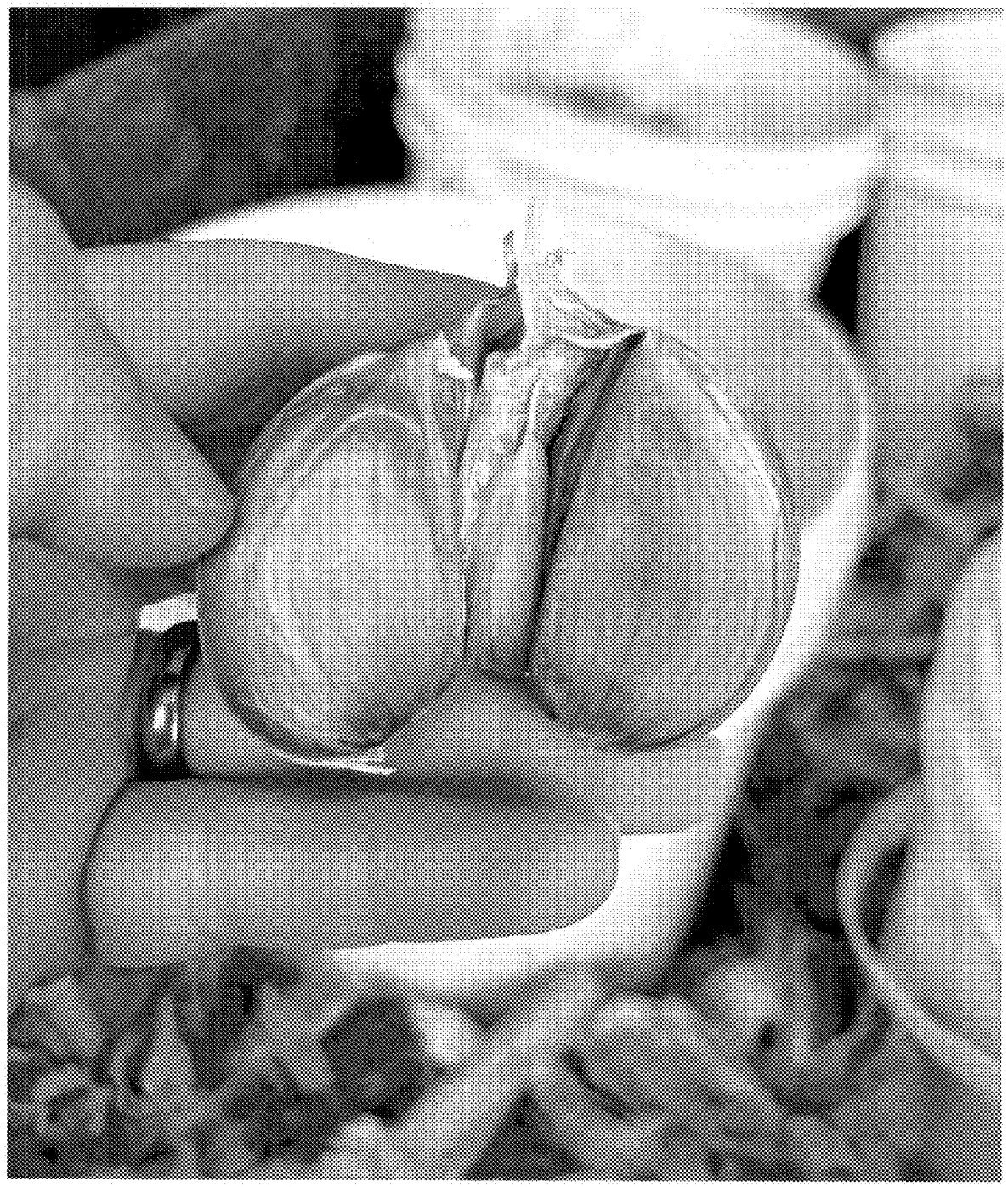
FIG. 4: A partial cluster of cloves after fully cured, demonstrating the clove color and size variation.
Figure 5:
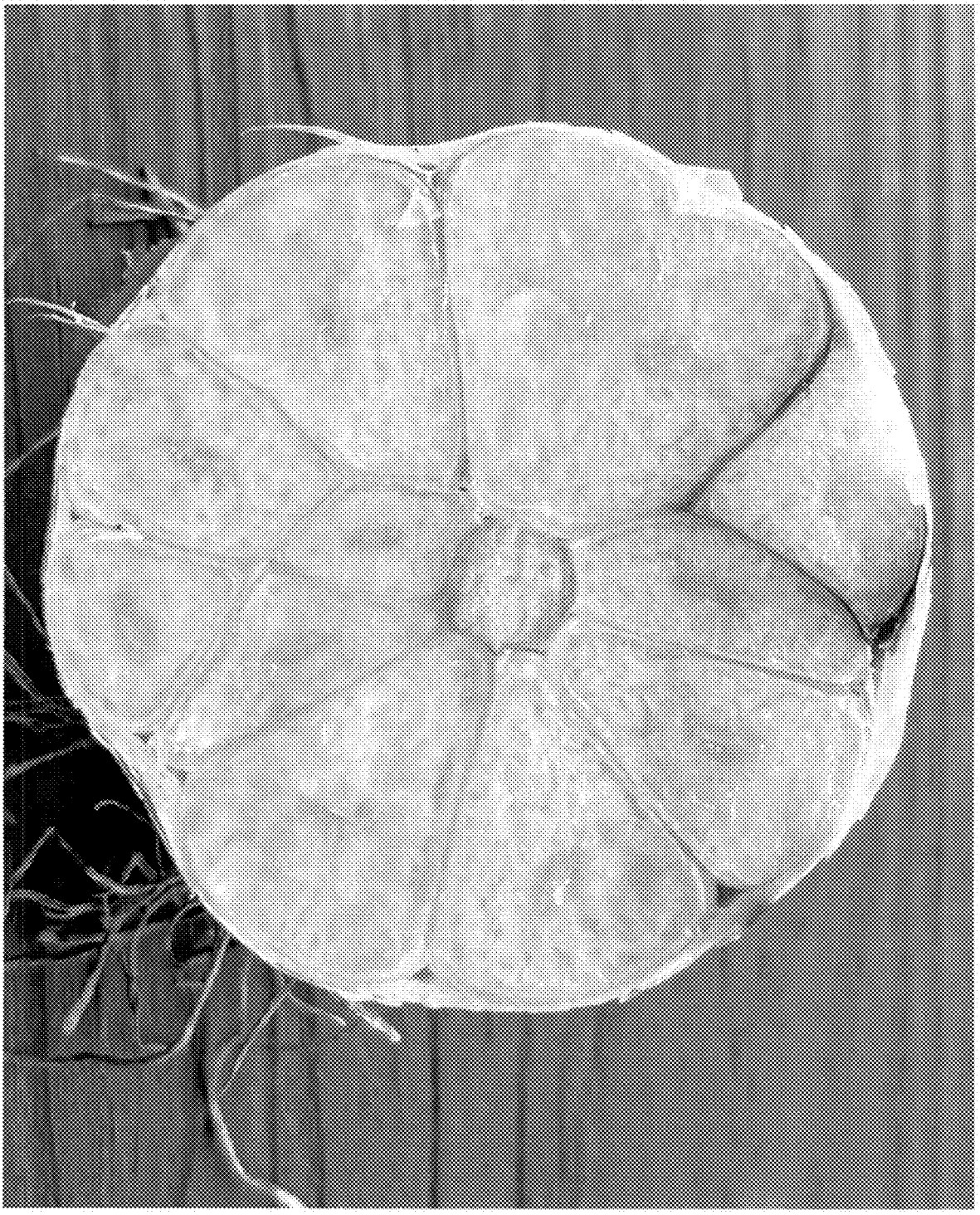
FIG. 5: A horizontal slice of a bulb of 'Slamka', 9.5 months after planting, showing the arrangement of 11 individual cloves of varying size.
Figure 6:
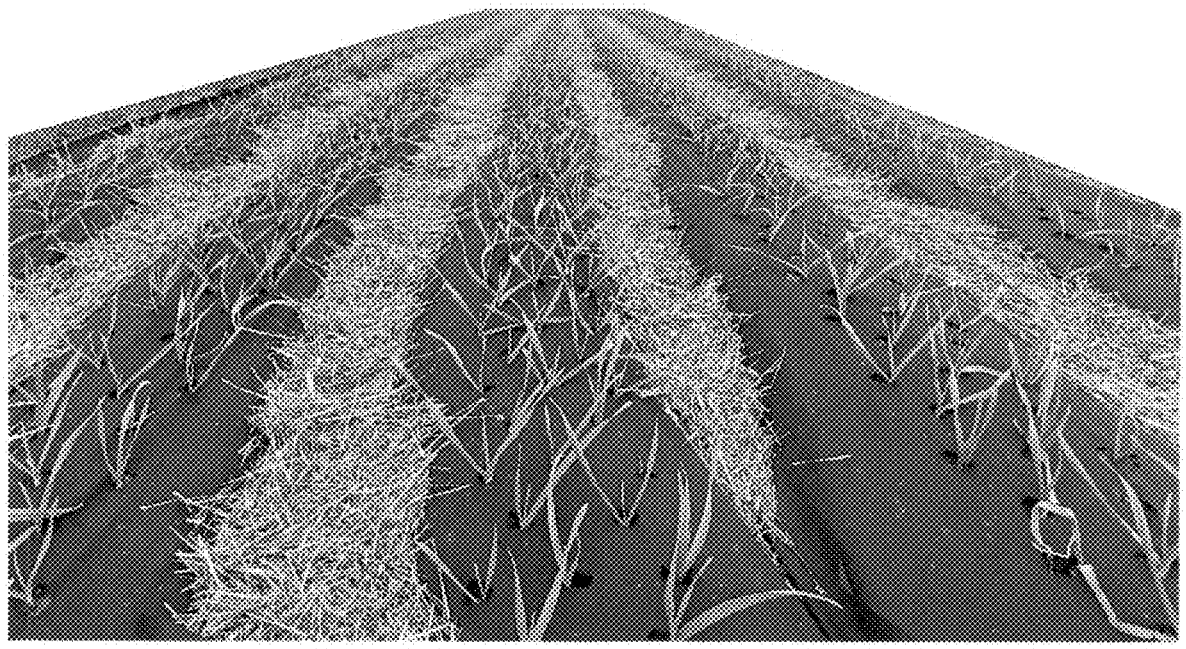
FIG. 6: 'Slamka' vegetation 4 weeks after planting.
Figure 7:
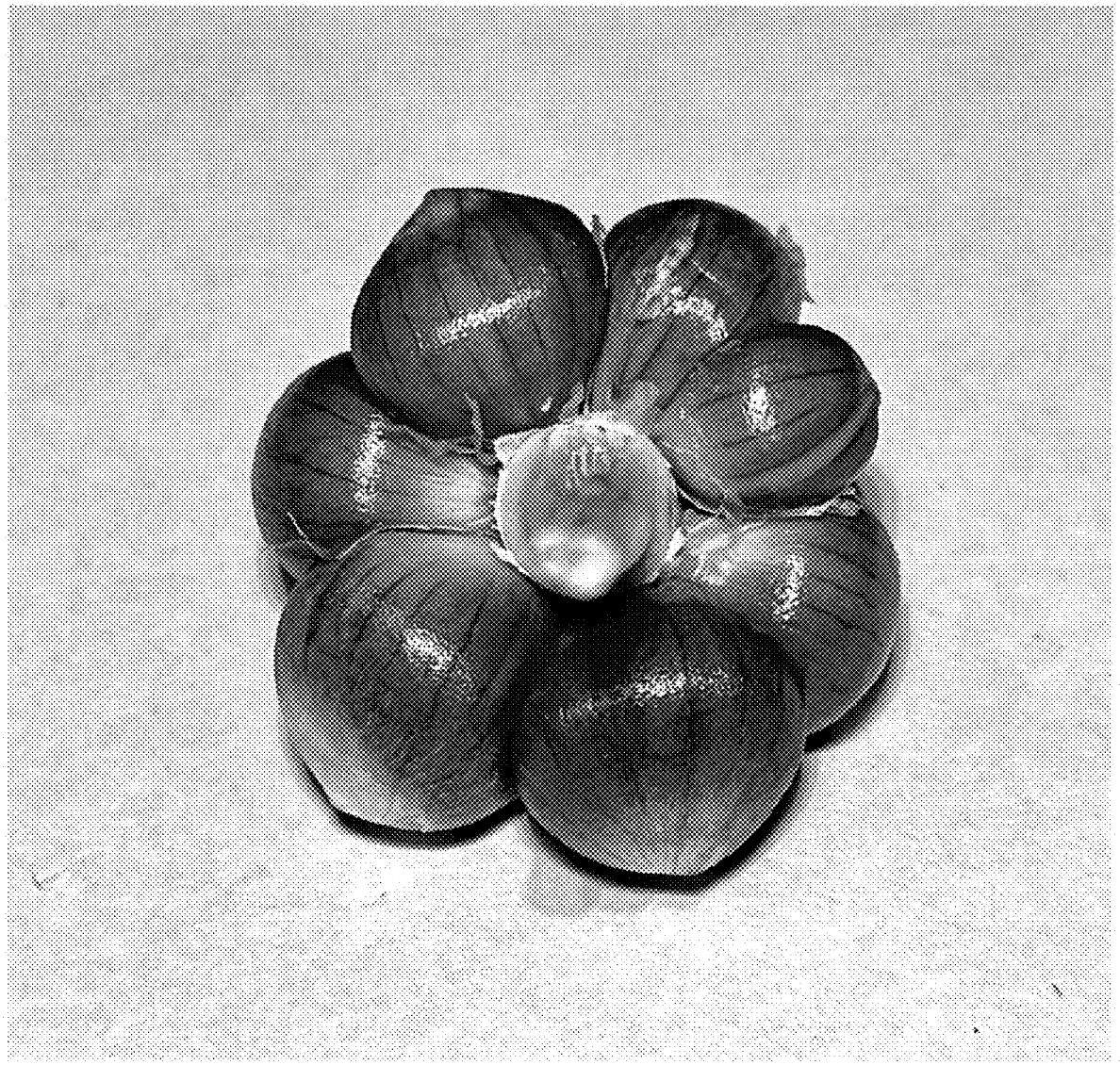
FIG. 7: Umbel with spathe removed, inferior view, showing bulbils with vertical striping. 10 months after planting.
Figure 8:
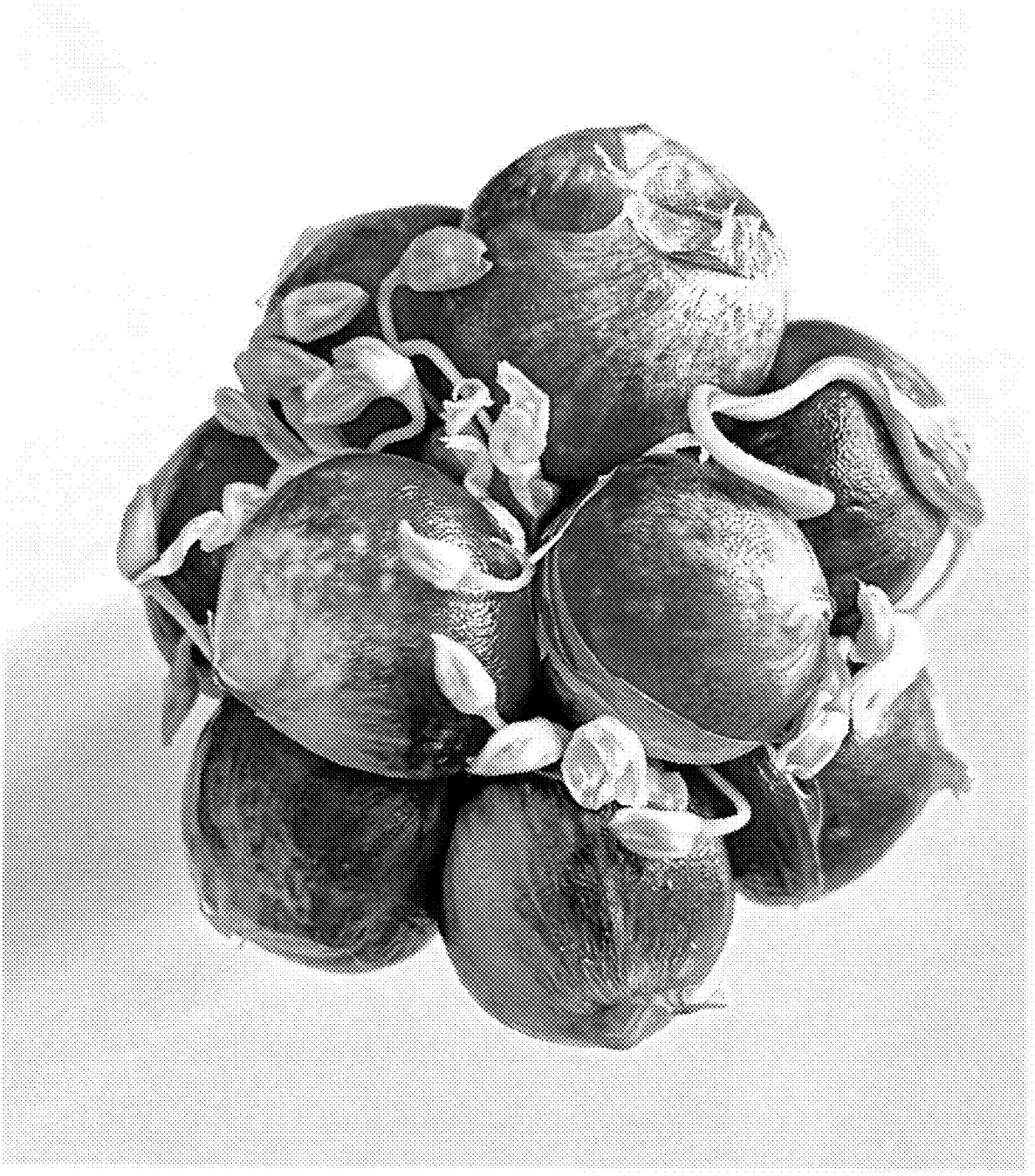
FIG. 8: Umbel with spathe removed, superior view, showing bulbil cluster, flowers, and stems. 10 months after planting.
Figure 9:
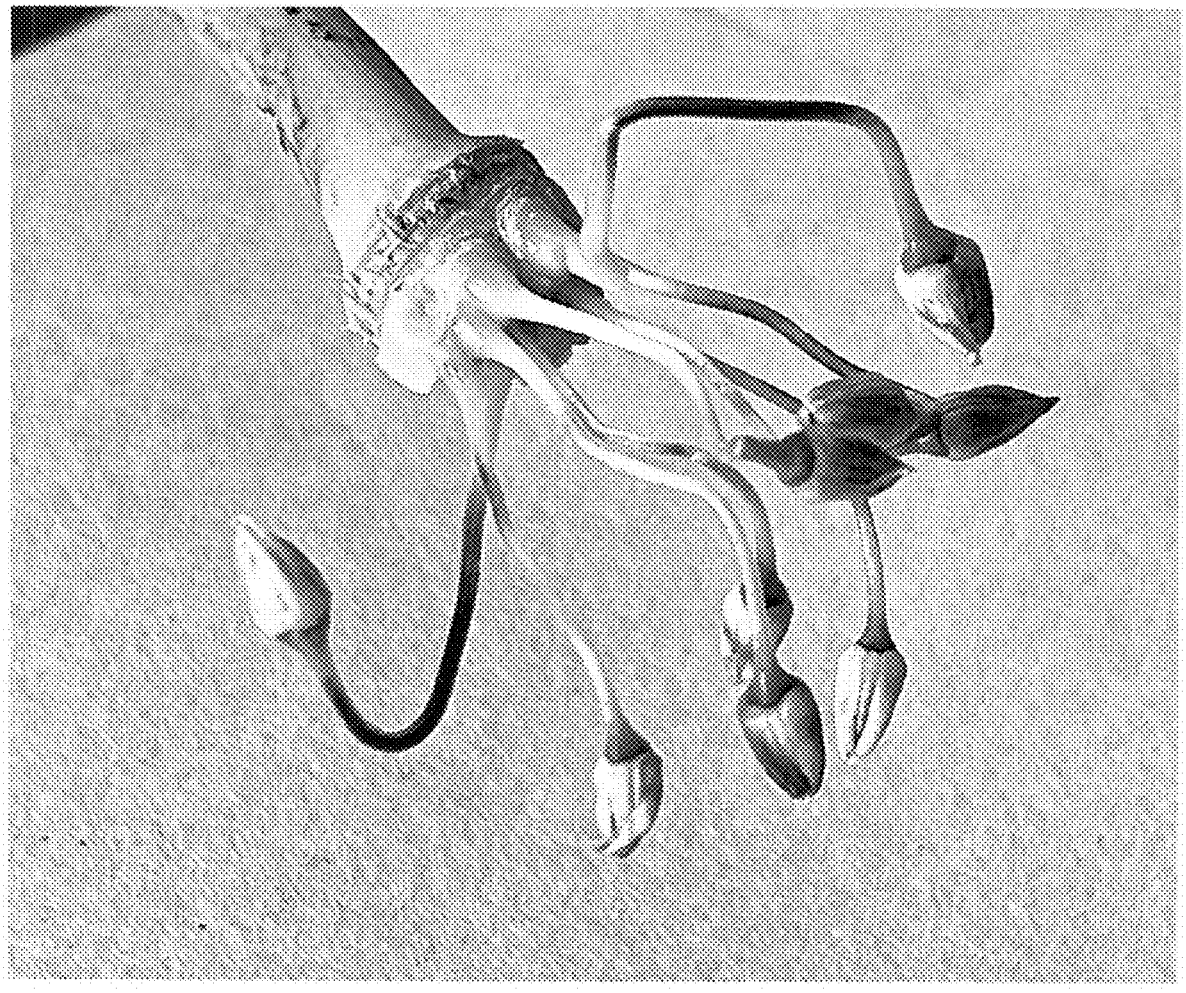
FIG. 9: Flowers on stem with bulbils removed. 10 months after planting.
Figure 10:
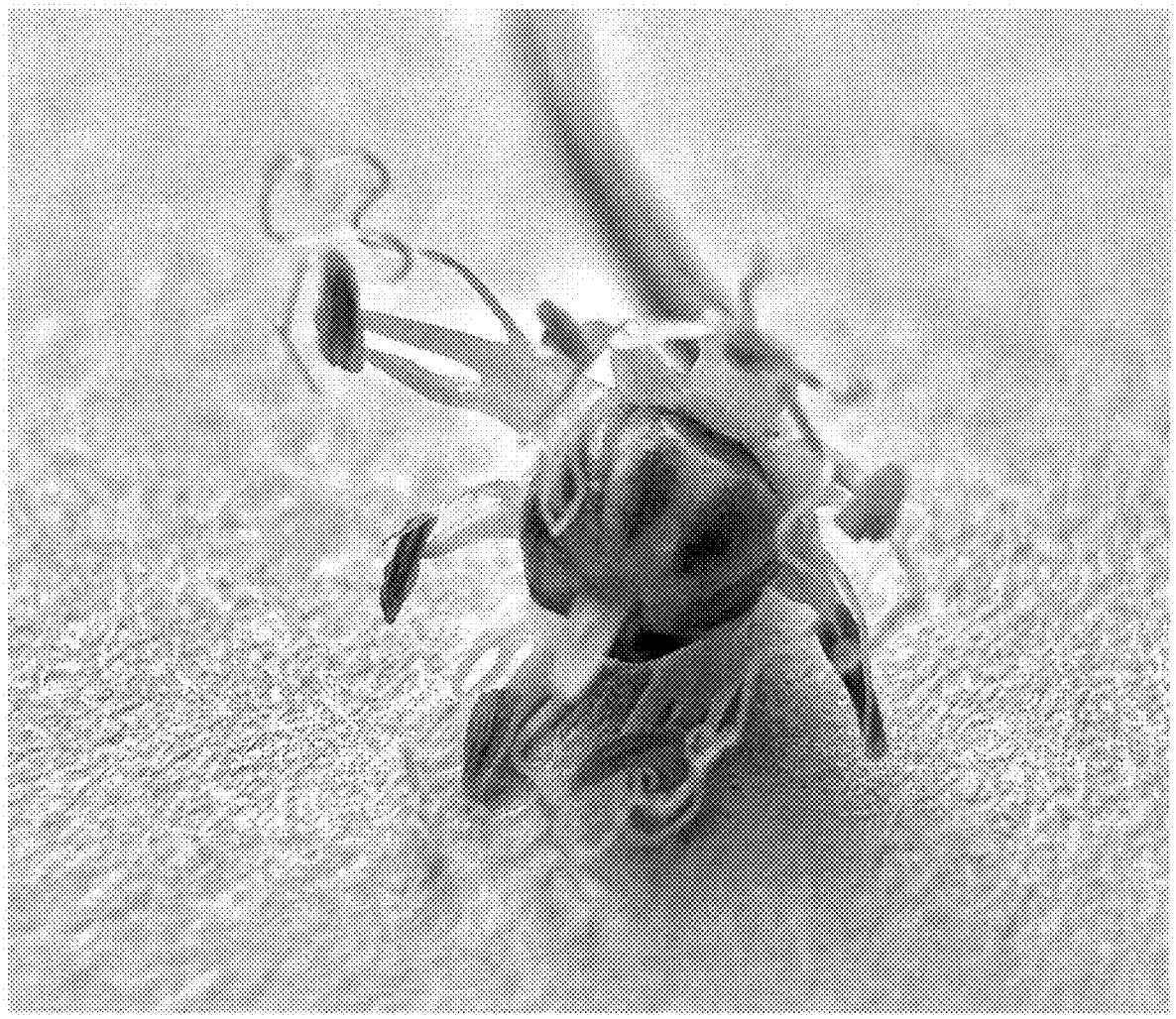
FIG. 10: Flower with tepals removed. 10 months after planting.
Figure 11:
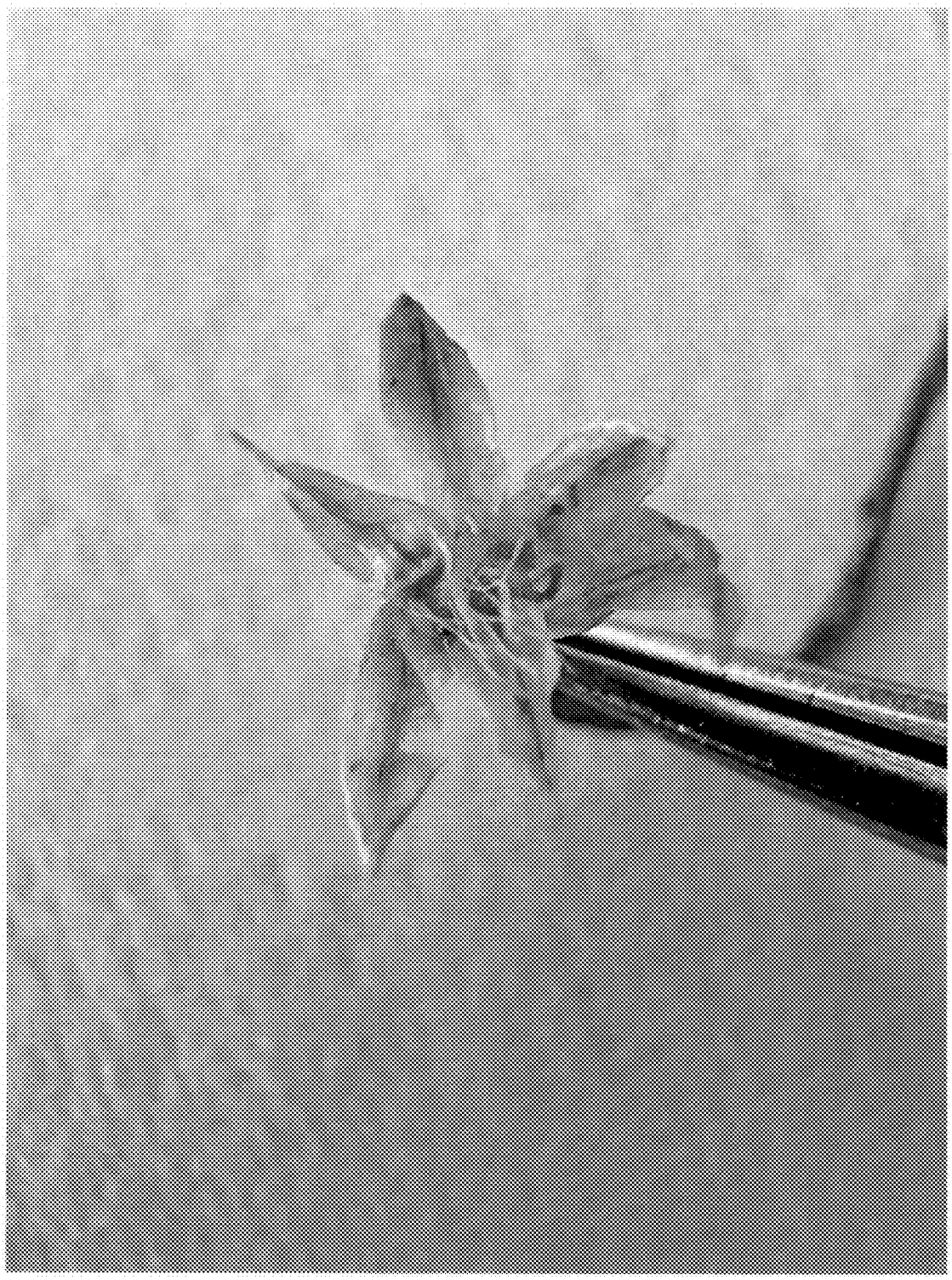
FIG. 11: Flower with tepals opened. 10 months after planting.
Figure 12:
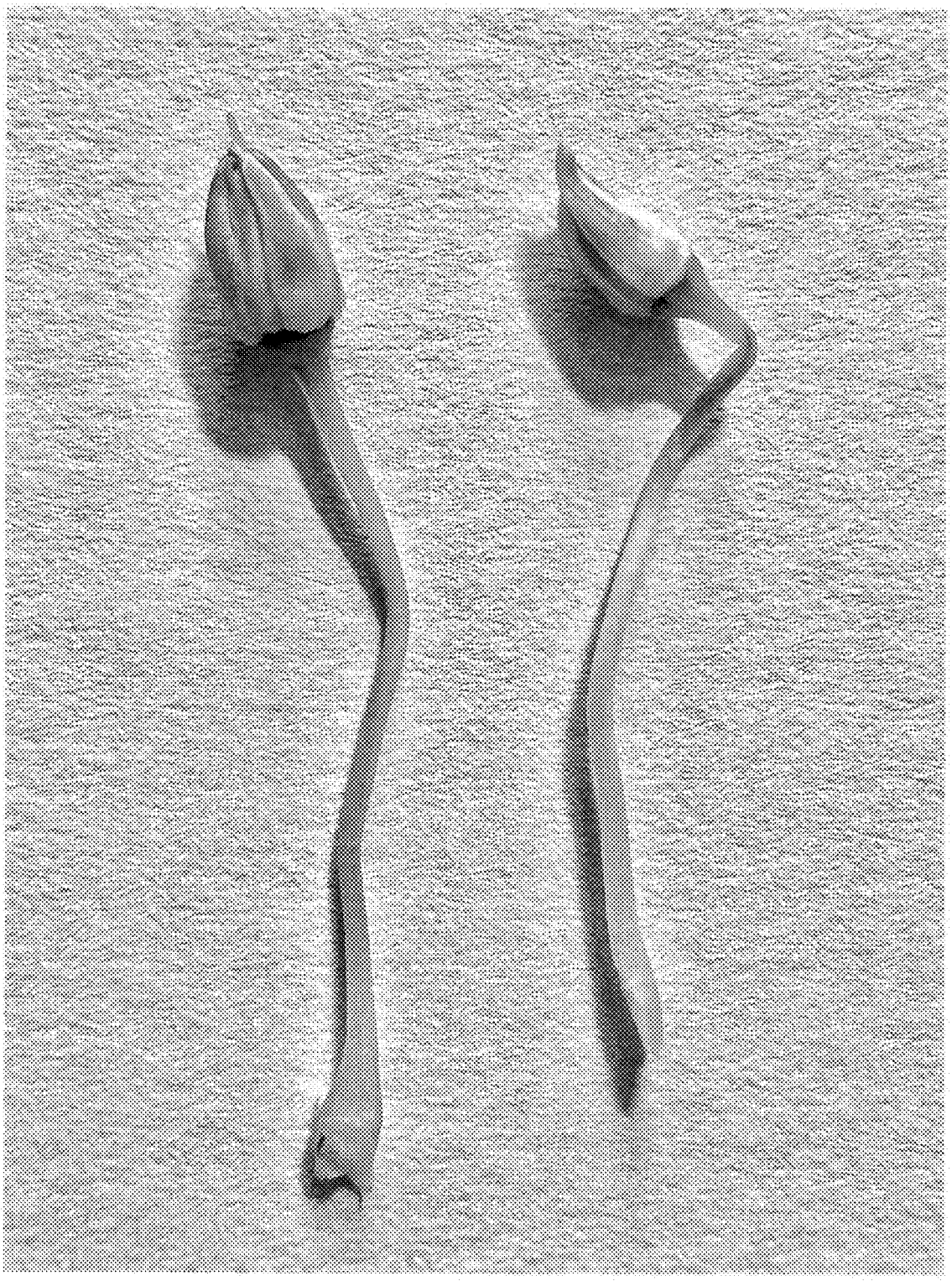
FIG. 12: Flowers on pedicels, 10 months after planting.
Figure 13:
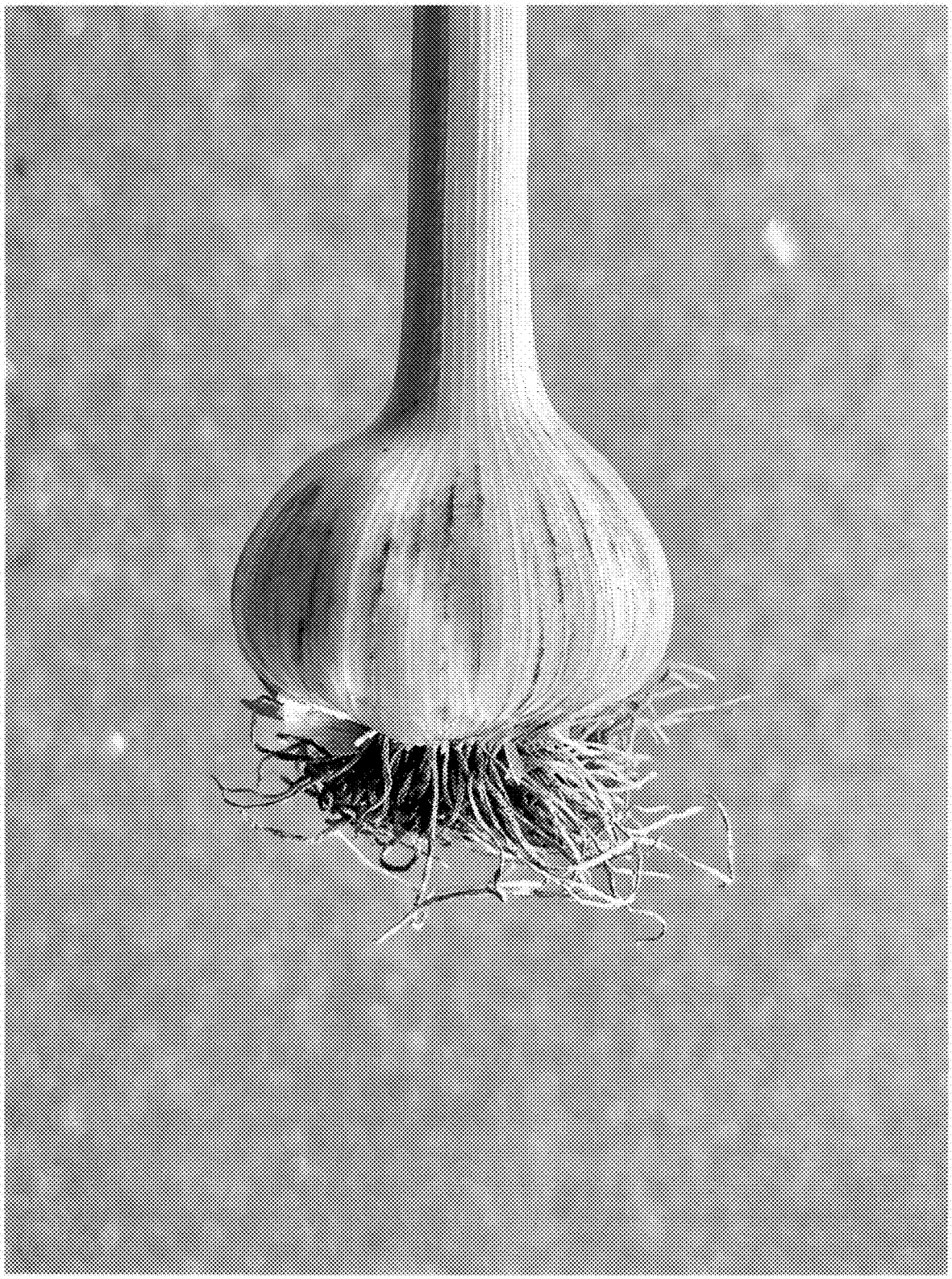
FIG. 13: Garlic Bulb with trimmed roots, showing bulb skin color with purple streaking. 9.5 months after planting.
Figure 14:
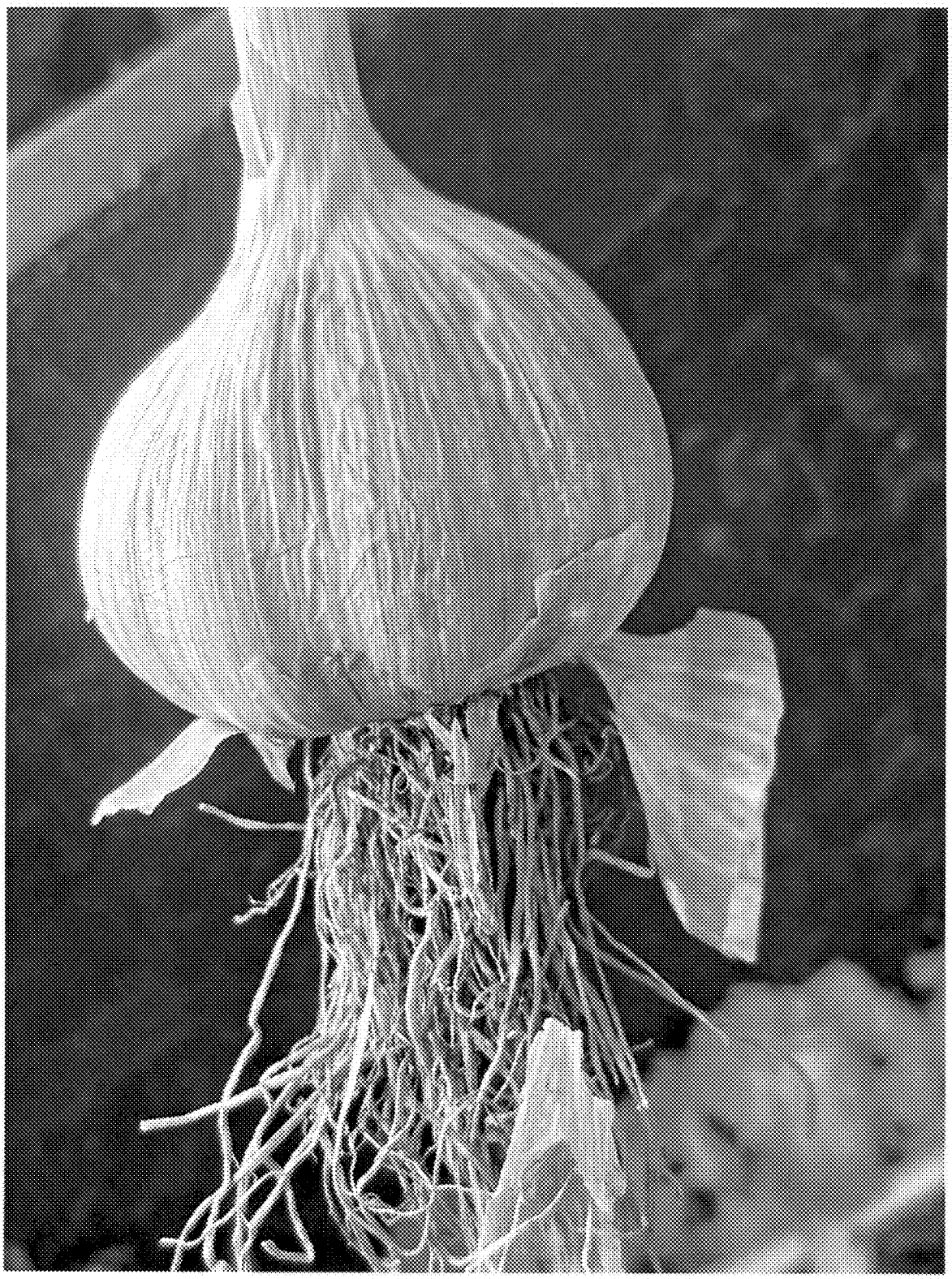
FIG. 14: Garlic bulb after curing, showing dry, off-white outer bulb skin layer with purple hues.
Figure 15:
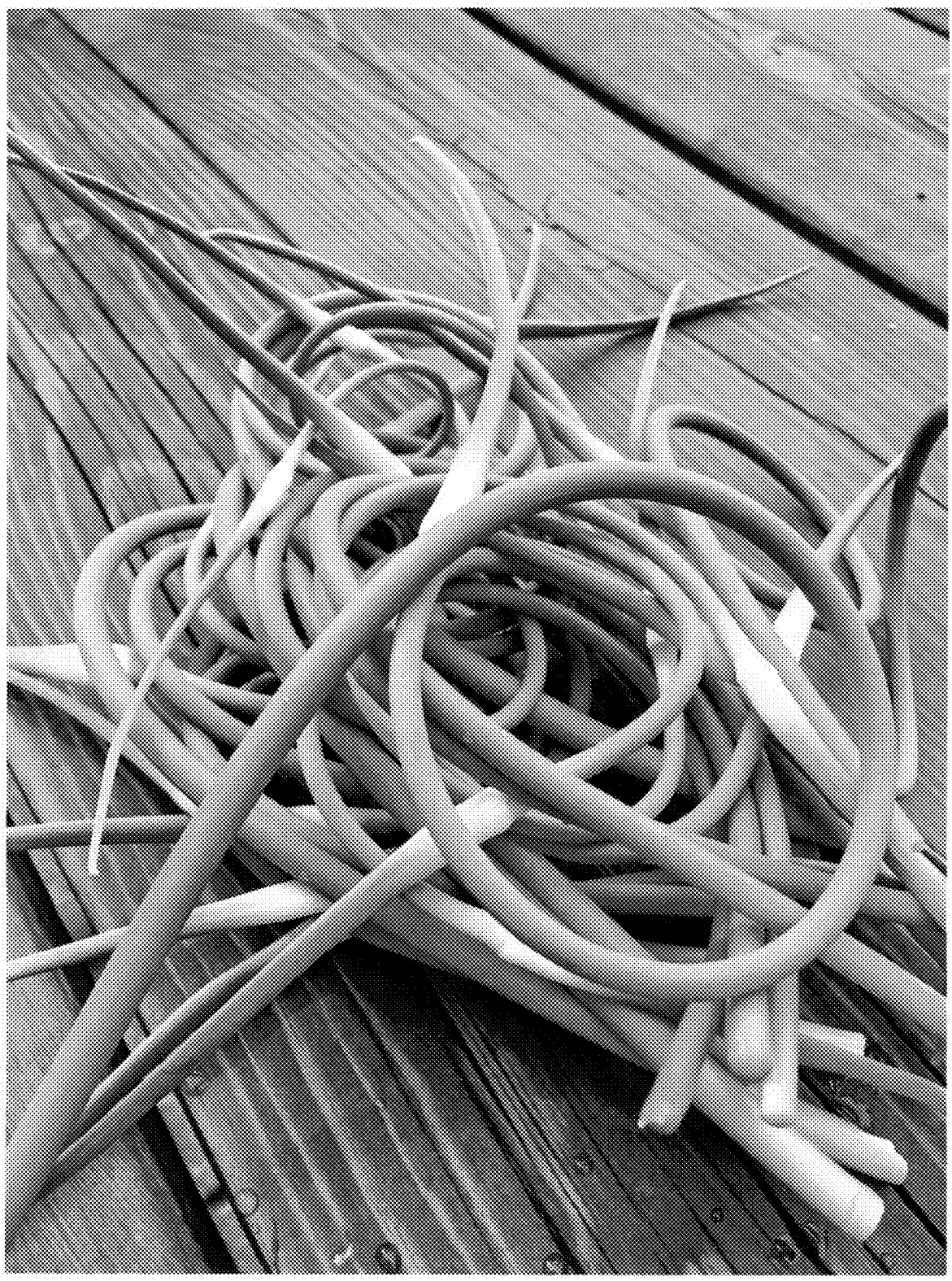
FIG. 15: Harvested scapes showing coloring and curvature.
Figure 16:
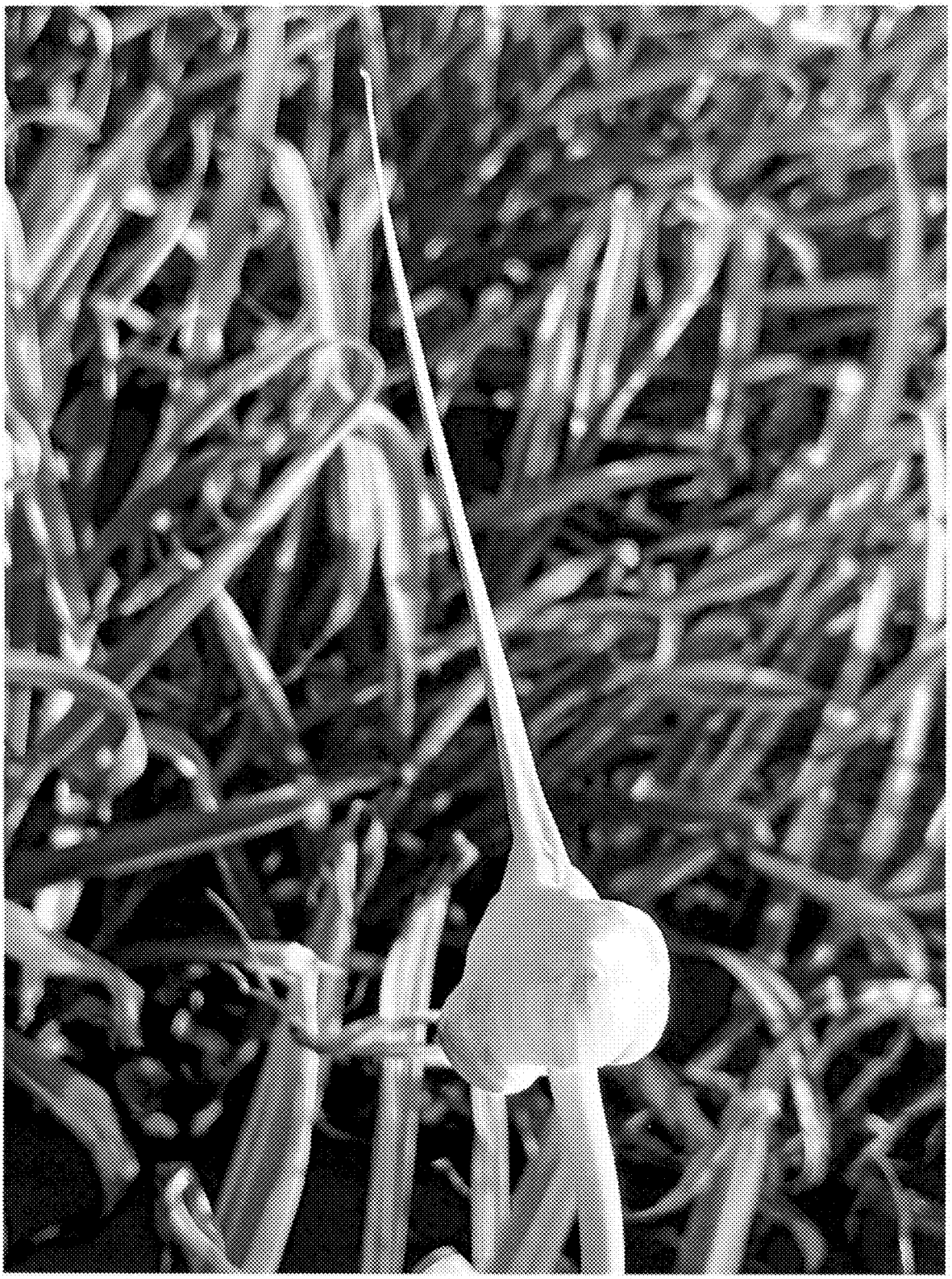
FIG. 16: Scape topset.

The characteristics of 'Slamka' may vary depending on environmental factors such as temperature, light intensity, day length, soil composition, or storage conditions, while maintaining consistent genetic traits. It is important to note that 'Slamka' has not been evaluated under all conceivable environmental conditions. The following data was collected during the 2023-2024 Southeastern Wisconsin growing season.

Asexual Reproduction

The claimed garlic plant variety 'Slamka' has been asexually reproduced by vegetative propagation using cloves in Southeastern Wisconsin, including Oak Creek, Wisconsin, and Franksville, Wisconsin. After several successive generations of asexual reproduction by cloves, the distinctive characteristics of the claimed plant variety have been shown to be stable and reproduced true to type.

Classification and Comparison with Known Varieties

The claimed plant variety 'Slamka' is classified as a bolting hardneck garlic (*Allium sativum* var. *ophioscorodon*) based on a correlated set of anatomical and reproductive characteristics that distinguish hardneck garlic from non-bolting softneck forms.

The claimed variety consistently produces a true flowering scape arising from the center of the plant and terminating in a spathe-enclosed umbel. The umbel bears vegetative bulbils and occasional flowers with identifiable floral structures, including tepals, stamens, and ovary tissue. The consistent formation of a scape-borne inflorescence is a defining reproductive feature of bolting garlic morphotypes and is not characteristic of softneck garlic varieties.

Following maturity and curing, bulbs of the claimed variety exhibit a persistent central axis extending through the bulb, representing the lignified remnant of the scape and associated pseudostem tissue. This axis dries into a rigid, woody "hard neck," a structural hallmark of hardneck garlic. Softneck garlic varieties lack this lignified central axis and instead develop a pliable neck structure.

Bulbs of the claimed variety exhibit clove organization radially disposed about the persistent central axis, without the formation of multiple concentric clove layers characteristic of softneck garlics. While individual clove size and spacing may vary, the cloves are arranged primarily in a single radial tier surrounding the central stalk, consistent with hardneck bulb architecture.

Based on these correlated anatomical and reproductive traits, the claimed variety 'Slamka' is classified as a hardneck garlic.

Within the hardneck garlic groups, the claimed variety exhibits morphological and agronomic characteristics most consistent with the Purple Stripe group, and more particularly aligns with the Marbled Purple Stripe (MPS) subgroup. This classification is supported by the presence of purple-mottled bulb wrapper coloration, strongly bolting scapes, mid-season maturity, cold-climate adaptation, long storage life consistent with Marbled Purple Stripe garlics, and clove architecture characteristic of Purple Stripe types.

Although aligned with Marbled Purple Stripe garlics, the claimed variety 'Slamka' is distinguished from known MPS cultivars by the combination and degree of expression of its traits.

Commonly known Marbled Purple Stripe varieties, including Bogatyr, Metechi, Russian Red, Siberian, Nordic, Duganski, and Estonian Red, are generally characterized by vigorous growth, strong flavor, cold hardiness, and purple-marbled bulb wrappers. These varieties often exhibit lower clove counts per bulb, with more moderated internal clove size variation, and umbels bearing greater numbers of medium-sized bulbils.

The claimed variety 'Slamka' is further characterized by the following combination of traits:

- Larger average bulb size combined with intermediate-to-high clove counts relative to typical MPS cultivars;
- Pronounced intra-bulb clove size heterogeneity, including dominant cloves substantially larger than adjacent cloves, resulting in asymmetrical internal bulb structure;

Lower bulbil counts per umbel combined with unusually large individual bulbils;

Tall plant stature and thick pseudostem development;

Scapes that initially curl and then straighten with maturity;

Long storage life;

High productivity under low-input cultivation, with stable expression of these traits following successive asexual reproduction by cloves.

While individual characteristics of the claimed variety may overlap with those observed in known Marbled Purple Stripe cultivars, no single known variety exhibits this specific combination of plant stature, bulb size, clove count, clove size heterogeneity, bulbil morphology, and productivity.

Based on the foregoing botanical classification and comparative analysis, the claimed variety 'Slamka' is properly classified as a hardneck garlic of the Marbled Purple Stripe group and is new and distinct from known Marbled Purple Stripe garlic varieties. The unique combination and degree of expression of its anatomical, reproductive, and agronomic traits distinguish the claimed variety from its closest known relatives and support its recognition as a new and distinct garlic plant variety.

Botanical Description

Common name: Garlic.

Scientific name: *Allium sativum* var. *ophioscorodon.*

Family: Amaryllidaceae.

Subfamily: Allioideae.

Genus: *Allium.*

Species: *Allium sativum.*

Variety: *Ophioscorodon.*

Variety denomination: 'Slamka'.

Growth Habit: Erect.

Clove: The clove exhibits good peeling ability.

Scape: Present. Curvature when young and straightens during maturation. Topset: Oblong and globular umbel.

Bulbils: Large. Shape: Ellipsoidal.

Flowers: Small. Anthesis may not occur by the time of harvest.

Roots: Develop prior to winter, forming dense, fibrous root structures.

Color Characteristics

The following color descriptions are based on The Royal Horticultural Society Colour Chart (6th Edition), with color designations expressed as approximate matches. Color expression may vary with environmental conditions and tissue translucency.

Mature leaves:

*Upper surface.*—Green, corresponding most closely to RHS Green Group N138A, with color variation under differing light conditions, leaf orientation, and environmental factors, occasionally appearing lighter or darker than the anchor reference.

*Lower surface.*—Green, substantially similar to the upper surface, corresponding most closely to RHS Green Group N138A, with comparable apparent variation under differing light conditions.

Bulb:

*Bulb skin* (*outer wrapper*).—Off-white to pale buff, corresponding most closely to RHS Greyed-White Group 156A-156D. The outer wrapper exhibits longitudinal purple streaking and mottling.

*Streaking coloration.*—Greyed lavender-purple to purple, most closely corresponding to RHS Purple Group N87B, with apparent variation into adjacent purple groups due to uneven pigment distribution and tissue translucency. The coloration appears as longitudinal streaks and irregular mottling rather than uniform pigmentation.

Cloves:

*Clove skin.*—Light brown to medium brown, translucent, corresponding most closely to RHS Greyed-Orange Group 165B-165C, with occasional diffuse subsurface purplish blush or faint streaking visible through the outer skin layers, most closely corresponding to RHS Purple Group N77B.

*Clove flesh.*—Off-white, corresponding most closely to RHS White Group 155D.

Scape: Green, corresponding most closely to RHS Green Group N138A, with apparent color variation under differing light conditions and scape orientation, generally consistent with the coloration of the mature leaves.

Spathe: White to off-white, corresponding most closely to RHS White Group 155A-155D, occasionally exhibiting faint purple tinges corresponding most closely to RHS Purple Group N77B.

Beak: Green, similar to the scape, corresponding most closely to RHS Green Group N138A-N138D.

Bulbils:

*Bulbil skin* (*ground color*).—Greyed-red, corresponding most closely to RHS Greyed-Red Group 178A-178B.

*Bulbil striping.*—Distinct, sharply defined longitudinal stripes darker than the surrounding skin, corresponding most closely to RHS Purple Group N77A.

Pedicels: Light yellow-green, corresponding most closely to RHS Yellow-Green Group 145B-145D, with very faint, localized purple suffusion occasionally visible near bends or attachment points, corresponding most closely to RHS Purple Group N77D.

Flowers:

*Tepals* (*upper and lower surfaces*).—Narrow and translucent, predominantly white, corresponding most closely to RHS White Group NN155D, with very pale pink-purple pigmentation corresponding most closely to RHS Purple Group N77B, particularly along the midvein and toward the tips.

Cultivation Details

Climate adaptability: Particularly suited to the temperate climate of Southeastern Wisconsin, withstanding cold winters and warm summers. The performance of 'Slamka' in other climates has not been tested, and its adaptability outside of Southeastern Wisconsin remains uncertain.

Soil preference: Prefers well-drained soil.

Planting period: Typically planted in late summer through early fall.

Harvesting period: Typically harvested in summer, around July, approximately 10, months after planting.

Growth: Sprouts appear approximately 14 days after planting.

Storage life: Exhibits a long storage life, which can exceed 9 months under optimal conditions (cool, dry, and well-ventilated storage).

Light: Full sunlight.

Soil additions: Occasional organic material (such as manure or compost) may be added in some years, without a set schedule or testing.

Hardiness: The claimed garlic variety has demonstrated robust overwintering performance and normal vegetative growth under field conditions in Southern Wisconsin (USDA Plant Hardiness Zone 5B), where sub-zero winter temperatures occur. This region is also characterized by wide seasonal temperature variation. These observations are based on field performance within USDA Plant Hardiness Zone 5B and do not imply performance outside of this zone.

Disease and Pest Observations

During multiple growing seasons under standard field conditions in Southeastern Wisconsin, the claimed garlic variety 'Slamka' was observed for the presence of disease and pest symptoms. No observable symptoms of disease or pest infestation were detected on plants grown under normal cultural practices.

Specifically, no visible symptoms consistent with white rot (*Sclerotium cepivorum*), vegetable rot (*Penicillium, Mucor*, or *Rhizopus* spp.) *Fusarium* bulb rot (*Fusarium proliferatum*), basal rot (*F. culmorum, F. oxysporum*), *Botrytis* neck rot (*Botrytis porri*), downy mildew (*Peronospora destructor*), *Embellisia* skin blotch (*Embellisia allii*), purple blotch (*Alternaria porri*), rust (*Puccinia allii*), onion yellow dwarf virus, or leek yellow stripe virus were observed.

Additionally, no visible damage or symptoms attributable to stem and bulb nematode (*Ditylenchus dipsaci*), wireworms, leek moth, western flower *thrips*, onion *thrips* (*Thrips tabaci*), leafminers (*Liriomyza* spp.), bulb mites (*Rhizoglyphus* spp. or *Tyrophagus* spp.), or blister beetles were observed.

Observations were based on external plant appearance, foliage condition, bulb integrity at harvest, and cured bulb quality. The absence of symptoms reflects field observations only and does not imply resistance under all conditions or against all pathogens or pests.

Plant Characteristics

Total plant height: Mean 90.5 cm.

Bulb characteristics:

- *Diameter*.—Can exceed 7.5 cm, with a mean of 7.1 cm.
- *Height*.—Mean 4.7 cm.
- *Weight*.—Can exceed 150 grams, with a mean of 105 grams.
- *Bulb shape* (*side view*).—Circular.
- *Position of cloves at bulb tip*.—At the same level.
- *Bulb position of root disc*.—Flat.
- *Bulb shape at base*.—Rounded.
- *Bulb anthocyanin stripes on dry external scales*.—Present; appearing as irregular longitudinal anthocyanin striping beneath the outer dry scales, variable in intensity among bulbs.
- *Ground color of dry external scales*.—Yellowish white.

Clove characteristics:

- *Number of cloves per bulb*.—Variable. Typically, 8-14.
- *Clove size*.—Variable, can exceed 4.5 cm in width.
- *Flavor profile*.—Spicy, aromatic, bold, zesty, and rich.
- *Clove shape*.—Ovoid to wedge-shaped; asymmetrical due to radial packing within the bulb.
- *Clove length*.—Variable; individual cloves extend from the root disc to the bulb tip, with length generally corresponding to overall bulb height and exhibiting wide intra-bulb variation.
- *Clove distribution*.—Radial.
- *Clove intensity of color of scale*.—Medium.
- *Clove anthocyanin stripes on scale*.—Present.

Pseudostem characteristics:

- *Circumference at base*.—6.5 cm-8.5 cm, with a mean of 7.8 cm.
- *Anthocyanin coloration at pseudostem base*.—Absent.

Leaf characteristics:

- *Top leaf length*.—Mean 44.7 cm.
- *Second leaf length*.—Longer than the top leaf.
- *Bottom leaf width*.—Mean width 4.8 cm.
- *Top leaf width*.—Mean 2.4 cm.
- *Number of leaves*.—Typically, 9-11, with an average of 10.
- *Plant spread*.—Approximately 64 cm, measured as the horizontal distance across the outermost leaf tips of a mature plant when laid flat.
- *Leaf shape* (*cross section*).—Slightly concave along the leaf blade, with leaves conduplicate near the base and flattening distally.
- *Leaf apex shape*.—Acuminate, tapering gradually to a narrow tip.
- *Leaf surface texture*.—Upper and lower surfaces smooth and matte, lacking pubescence or waxy bloom.
- *Leaf fragrance*.—Garlic aroma present when leaves are crushed or bruised.

Root characteristics:

- *Root length*.—Approximate mean 16 cm, can exceed 20 cm.

Scape characteristics:

- *Length*.—Can exceed 75 cm, mean 61.5 cm.
- *Diameter at base*.—Mean 7.5 mm.
- *Topset height*.—Mean 17.6 cm.
- *Spathe opening*.—About half are open 10 months after planting.
- *Umbel width*.—Mean 4.4 cm.
- *Umbel height*.—Mean 2.4 cm.
- *Spathe beak length*.—Mean 15.2 cm.
- *Number of bulbils*.—Mean 8 bulbils per umbel.
- *Bulbil weight*.—Mean 12.4 g/bulbil.
- *Bulbil height*.—Mean 15.7 mm.
- *Bulbil width*.—Mean 15 mm, bulbil width can exceed 2 cm.
- *Flowers*.—Average 10 per umbel and 6 tepals per flower, mean tepal length 4.8 mm.
- *Pedicel*.—Mean length 18.3 mm.
- *Stamen*.—Average 6.5 per flower, mean length 2.2 mm.
- *Anther length*.—Mean 1.3 mm.
- *Ovary height*.—Mean 1.7 mm.
- *Ovary width*.—Mean 1.5 mm.

Productivity:

- *Yield*.—Approximately 87,700 bulbs per acre, corresponding to a total yield of approximately 9,200 kg per acre, as extrapolated from observed plot yields under current cultivation practices.

Shipping quality and market use: The claimed garlic variety is intended for fresh market and culinary use, Culinary applications include, but are not limited to, use as a seasoning and in sautés, roasts, soups, breads, pastas, pesto, pickling, stir-frying, marinades, and the production of black garlic. The variety has been observed to exhibit a long storage life, consistent with hardneck MPS garlic types, with bulbs remaining in storage for greater than nine months under cool, dry, and well-ventilated conditions. Shipping quality under commercial transport conditions has not been specifically evaluated.

The invention claimed is:

1. A new and distinct variety of *Allium sativum* var. *ophioscorodon* plant named 'Slamka', as illustrated and described herein.

* * * * *